(12) United States Patent
Chen et al.

(10) Patent No.: US 10,709,361 B2
(45) Date of Patent: Jul. 14, 2020

(54) METHODS AND SYSTEMS FOR CORRECTING BLOOD ANALYTE MEASUREMENTS

(71) Applicant: Senseonics, Incorporated, Germantown, MD (US)

(72) Inventors: Xiaoxiao Chen, Washington, DC (US); Andrew Dehennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 147 days.

(21) Appl. No.: 15/939,683

(22) Filed: Mar. 29, 2018

(65) Prior Publication Data

US 2018/0279923 A1    Oct. 4, 2018

Related U.S. Application Data

(60) Provisional application No. 62/478,859, filed on Mar. 30, 2017, provisional application No. 62/563,236, filed on Sep. 26, 2017.

(51) Int. Cl.
*A61B 5/1455* (2006.01)
*A61B 5/145* (2006.01)
(Continued)

(52) U.S. Cl.
CPC .......... *A61B 5/1451* (2013.01); *A61B 5/0031* (2013.01); *A61B 5/076* (2013.01);
(Continued)

(58) Field of Classification Search
None
See application file for complete search history.

(56) References Cited

U.S. PATENT DOCUMENTS 8,073,548 B2    12/2011  Colvin, Jr. et al.
9,414,775 B2     8/2016  Colvin, Jr. et al.
(Continued)

FOREIGN PATENT DOCUMENTS

EP    2 770 907 B1    7/2018
WO    2015/021273 A1  2/2015

*Primary Examiner* — Eric F Winakur
*Assistant Examiner* — Marjan Fardanesh
(74) *Attorney, Agent, or Firm* — Rothwell, Figg, Ernst & Manbeck, P.C.

(57) ABSTRACT

A system, transceiver, and method for calculating and correcting levels (e.g., analyte levels) in a first medium (e.g., blood) using measurements from a second medium (e.g., interstitial fluid). In some embodiments, a transceiver may calculate an initial second medium level. The transceiver may calculate an initial second medium level rate of change ("ROC") using at least the initial second medium level and past second medium level(s). The transceiver may calculate a first medium level using at least the initial second medium level and the initial second medium level ROC. The transceiver may calculate a subsequent second medium level. The transceiver may calculate an updated second medium level ROC using at least the initial second medium level, the subsequent second medium level, and past second medium level(s). The transceiver may calculate a corrected first medium level using at least the initial second medium level and the updated second medium level ROC.

34 Claims, 10 Drawing Sheets

(51) Int. Cl.
  *A61B 5/1459* (2006.01)
  *A61B 5/00* (2006.01)
  *A61B 5/1486* (2006.01)
  *A61B 5/07* (2006.01)
  *A61B 5/1473* (2006.01)

(52) U.S. Cl.
  CPC .......... *A61B 5/1459* (2013.01); *A61B 5/1473* (2013.01); *A61B 5/14503* (2013.01); *A61B 5/14532* (2013.01); *A61B 5/14546* (2013.01); *A61B 5/14556* (2013.01); *A61B 5/14865* (2013.01); *A61B 5/002* (2013.01); *A61B 5/742* (2013.01); *A61B 2560/0219* (2013.01); *A61B 2562/0257* (2013.01)

(56) References Cited

U.S. PATENT DOCUMENTS

| | | |
|---|---|---|
| 9,693,714 B2 | 7/2017 | DeHennis et al. |
| 9,839,383 B2 | 12/2017 | Hayter et al. |
| 10,028,686 B2 | 7/2018 | Hayter |
| 2009/0018425 A1 | 1/2009 | Ouyang et al. |
| 2013/0241745 A1 | 9/2013 | Colvin, Jr. et al. |
| 2016/0206233 A1* | 7/2016 | Hayter ............... A61B 5/14532 |
| 2016/0346457 A1 | 12/2016 | Jennewine |

* cited by examiner

METHODS AND SYSTEMS FOR CORRECTING BLOOD ANALYTE MEASUREMENTS

CROSS-REFERENCE TO RELATED APPLICATION

The present application claims the benefit of priority to U.S. Provisional Application Ser. No. 62/478,859, filed on Mar. 30, 2017, and U.S. Provisional Application Ser. No. 62/563,236, filed on Sep. 26, 2017, which are incorporated herein by reference in their entireties.

BACKGROUND

Field of Invention

The present invention relates to calculating and correcting levels in a first medium using measurements from a second medium. More specifically, aspects of the present invention relate to correcting first medium levels when new information becomes available. Even more specifically, aspects of the present invention relate to calculating blood analyte levels using measurements of interstitial fluid analyte levels and correcting the calculated blood analyte levels when one or more new measurements of interstitial fluid analyte levels become available.

Discussion of the Background

Analyte monitoring systems may be used to monitor analyte levels, such as analyte concentrations. One type of analyte monitoring system is a continuous glucose monitoring (CGM) system. A CGM system measures glucose levels throughout the day and can be very useful in the management of diabetes. Some analyte monitoring systems use measurements indicative of analyte levels in interstitial fluid ("ISF") to calculate ISF analyte levels and then convert the ISF analyte levels to blood analyte levels. The analyte monitoring systems may display the blood analyte levels to a user. However, because ISF analyte levels lag behind blood analyte levels, accurate conversion of ISF analyte levels to blood analyte levels is difficult.

SUMMARY

Aspects of the present invention relate to improving the accuracy of levels displayed to a user.

One aspect of the invention may provide an analyte monitoring system including an analyte sensor and a transceiver. The analyte sensor may include an indicator element that exhibits one or more detectable properties based on an amount or concentration of an analyte in proximity to the indicator element. The transceiver may be configured to receive first sensor data from the analyte sensor. The transceiver may be configured to calculate a first interstitial fluid analyte level using at least the first sensor data; calculate a first interstitial fluid analyte level rate of change using at least the first interstitial fluid analyte level and one or more past interstitial fluid analyte levels. The transceiver may be configured to calculate a first blood analyte level using at least the first interstitial fluid analyte level and the first interstitial fluid analyte level rate of change. The transceiver may be configured to, after receiving the first sensor data, receive second sensor data from the analyte sensor. The transceiver may be configured to calculate a second interstitial fluid analyte level using at least the second sensor data. The transceiver may be configured to calculate an updated first interstitial fluid analyte level rate of change using at least the first interstitial fluid analyte level, the second interstitial fluid analyte level, and the one or more past interstitial fluid analyte levels. The transceiver may be configured to calculate a corrected first blood analyte level using at least the first interstitial fluid analyte level and the first interstitial fluid analyte level rate of change.

In some embodiments, the transceiver may be further configured to: calculate a second interstitial fluid analyte level rate of change using at least the first and second interstitial fluid analyte levels; and calculate a second blood analyte level using at least the second interstitial fluid analyte level and the second interstitial fluid analyte level rate of change. In some embodiments, the system may further include a display device configured to: receive and display the first blood analyte level; receive and display the second blood analyte level; and receive and display the corrected first blood analyte level.

In some embodiments, the system may further include a display device configured to: receive and display the first blood analyte level; and receive and display the corrected first blood analyte level. In some embodiments, the display device may be configured to: display the first blood analyte level until the corrected first blood analyte level is received; and, after receiving the corrected first blood analyte level, display the corrected first blood analyte level instead of the first blood analyte level.

One aspect of the invention may provide a method of calculating and correcting blood analyte levels. The method may include using a transceiver to receive first sensor data from an analyte sensor. The method may include using the transceiver to calculate a first interstitial fluid analyte level based on at least the first sensor data. The method may include using the transceiver to calculate a first interstitial fluid analyte level rate of change based on at least the first interstitial fluid analyte level and one or more past interstitial fluid analyte levels. The method may include using the transceiver to calculate a first blood analyte level based on at least the first interstitial fluid analyte level and the first interstitial fluid analyte level rate of change. The method may include, after receiving the first sensor data, using the transceiver to receive second sensor data from the analyte sensor. The method may include using the transceiver to calculate a second interstitial fluid analyte level based on at least the second sensor data. The method may include using the transceiver to calculate an updated first interstitial fluid analyte level rate of change based on at least the first interstitial fluid analyte level, the second interstitial fluid analyte level, and the one or more past interstitial fluid analyte levels. The method may include using the transceiver to calculate a corrected first blood analyte level based on at least the first interstitial fluid analyte level and the first interstitial fluid analyte level rate of change.

One aspect of the invention may provide a transceiver including a sensor interface device and a processor. The sensor interface device may be configured to convey a power signal to an analyte sensor, receive first sensor data from the analyte sensor, and, after receiving the first sensor data, receive second sensor data. The processor may be configured to: calculate a first interstitial fluid analyte level using at least the first sensor data; calculate a first interstitial fluid analyte level rate of change using at least the first interstitial fluid analyte level and one or more past interstitial fluid analyte levels; calculate a first blood analyte level using at least the first interstitial fluid analyte level and the first interstitial fluid analyte level rate of change; calculate a second interstitial fluid analyte level using at least the second sensor data; calculate an updated first interstitial fluid analyte level rate of change using at least the first interstitial fluid analyte level, the second interstitial fluid analyte level, and the one or more past interstitial fluid analyte levels; and calculate a corrected first blood analyte level using at least the first interstitial fluid analyte level and the first interstitial fluid analyte level rate of change.

One aspect of the invention may provide a method of calculating and correcting levels in a first medium using measurements from a second medium. The method may include using a transceiver to calculate an initial second medium level based on at least initial measurement data. The method may include using the transceiver to calculate an initial second medium level rate of change based on at least the initial second medium level and one or more past second medium levels. The method may include using the transceiver to calculate a first medium level based on at least the initial second medium level and the initial second medium level rate of change. The method may include using the transceiver to calculate a subsequent second medium level based on at least subsequent measurement data. The method may include using the transceiver to calculate an updated second medium level rate of change based on at least the initial second medium level, the subsequent second medium level, and the one or more past second medium levels. The method may include using the transceiver to calculate a corrected first medium level based on at least the initial second medium level and the updated second medium level rate of change.

In some embodiments, the method may include using the transceiver to calculate a subsequent second medium level rate of change based on at least the initial and subsequent second medium levels. In some embodiments, the method may include using the transceiver to calculate a subsequent first medium level based on at least the subsequent second medium level and the subsequent second medium level rate of change. In some embodiments, the method may include using the transceiver to convey the first medium level to a display device; using the transceiver to convey the subsequent second medium level to the display device; and using the transceiver to convey the corrected first medium level to the display device.

In some embodiments, the method may include using the transceiver to convey the first medium level to a display device; and using the transceiver to convey the corrected first medium level to the display device. In some embodiments, the method may include using the display device to receive and display the first medium level; and using the display device to receive and display the corrected first medium level. In some embodiments, the method may include using the display device to display the first medium level until display device receives the corrected first medium level; and using the display device to, after receiving the corrected first medium level, display the corrected first medium level instead of the first medium level.

In some embodiments, the first medium may be blood. In some embodiments, the second medium may be interstitial fluid. In some embodiments, the initial second medium level may be an initial interstitial fluid analyte level.

One aspect of the invention may provide a monitoring system for calculating and correcting levels in a first medium using measurements from a second medium. The system may include a sensor and a transceiver. The sensor may be configured to take one or more measurements indicative of a level in the second medium. The transceiver may be configured to receive initial sensor data from the sensor. The initial sensor data may include one or more measurements indicative of an initial level in the second medium. The transceiver may be configured to calculate an initial second medium level using at least the initial sensor data. The transceiver may be configured to calculate an initial second medium level rate of change using at least the initial second medium level and one or more past second medium levels. The transceiver may be configured to calculate a first medium level using at least the initial second medium level and the initial second medium level rate of change. The transceiver may be configured to receive subsequent sensor data from the sensor. The subsequent sensor data may include one or more measurements indicative of a subsequent level in the second medium. The transceiver may be configured to calculate a subsequent second medium level using at least the subsequent sensor data. The transceiver may be configured to calculate an updated second medium level rate of change using at least the initial second medium level, the subsequent second medium level, and the one or more past second medium levels. The transceiver may be configured to calculate a corrected first medium level using at least the initial second medium level and the updated second medium level rate of change.

In some embodiments, the transceiver may be further configured to calculate a subsequent second medium level rate of change based on at least the initial and subsequent second medium levels and may be further configured calculate a subsequent first medium level based on at least the subsequent second medium level and the subsequent second medium level rate of change. In some embodiments, the transceiver may be further configured to: convey the first medium level to a display device, convey the subsequent second medium level to the display device, and convey the corrected first medium level to the display device.

In some embodiments, the transceiver may be further configured to convey the first medium level to a display device and may be further configured to convey the corrected first medium level to the display device. In some embodiments, the system may further comprise the display device, and the display device may be configured to: receive and display the first medium level; and receive and display the corrected first medium level. In some embodiments, the display device may be further configured to: display the first medium level until display device receives the corrected first medium level; and after receiving the corrected first medium level, display the corrected first medium level instead of the first medium level.

In some embodiments, the first medium may be blood. In some embodiments, the second medium may be interstitial fluid. In some embodiments, the initial second medium level may be an initial interstitial fluid analyte level.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
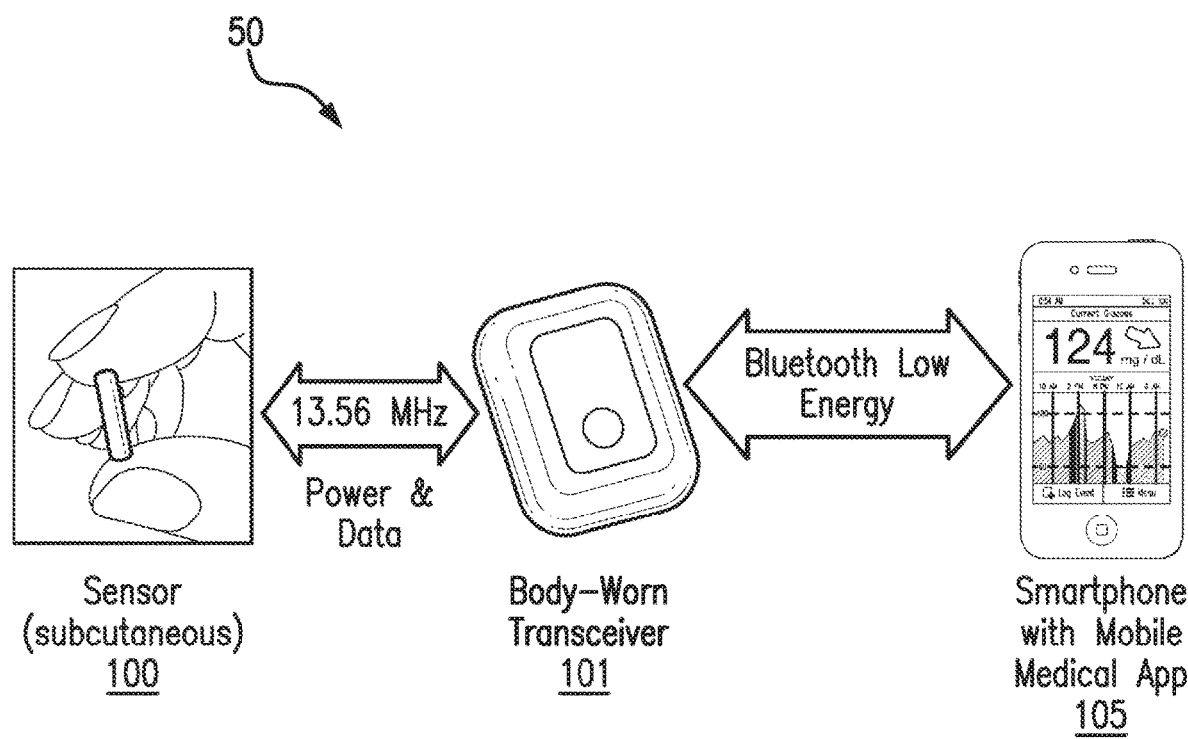
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, the analyte monitoring system 50 may include a web interface for plotting and sharing of uploaded data.

Figure 2:
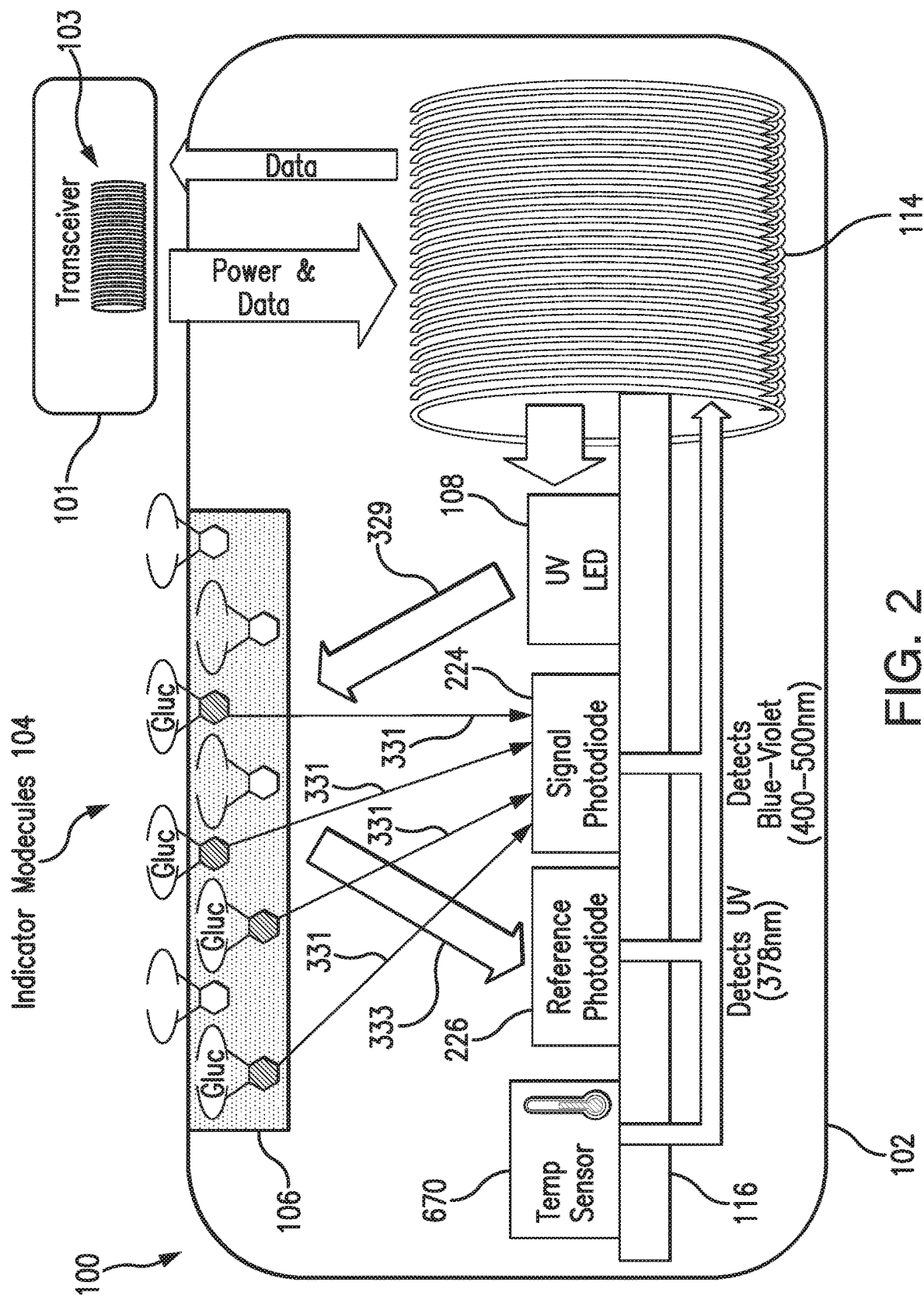
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) from the sensor 100. For example, in a non-limiting embodiment, the transceiver 101 may receive sensor data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
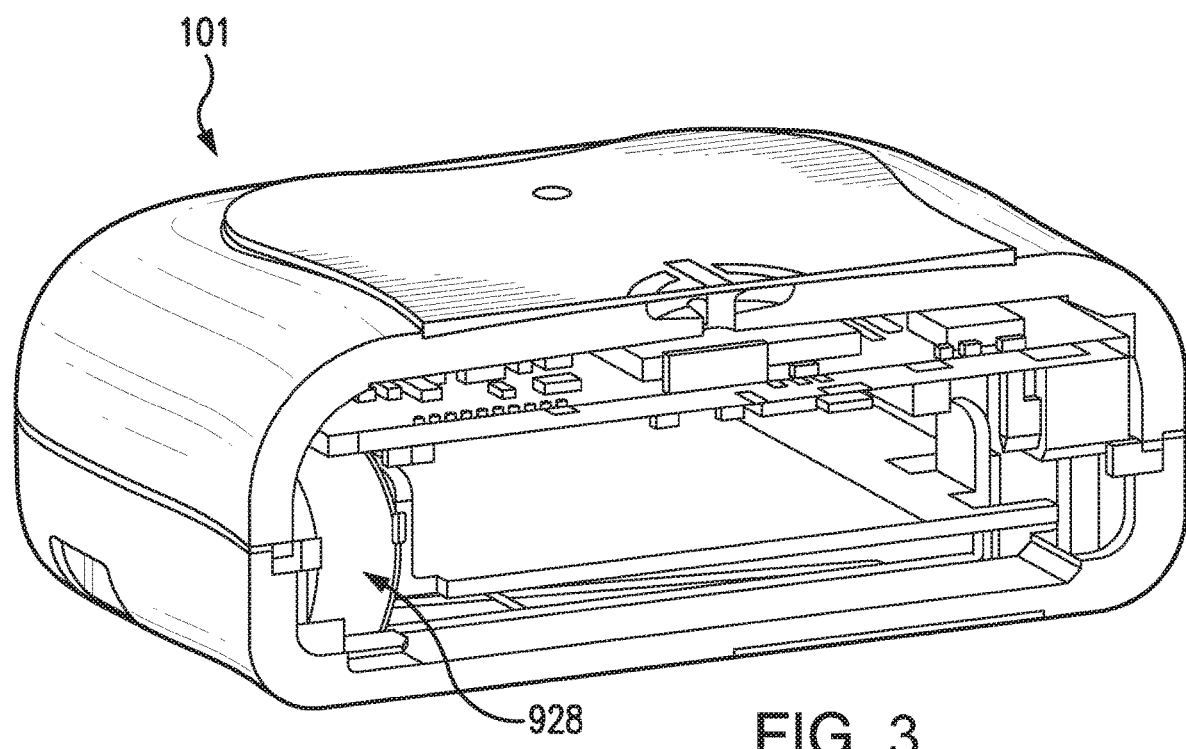
FIG. 3 is cross-sectional, perspective view of a transceiver embodying aspects of the invention.
Figure 4:
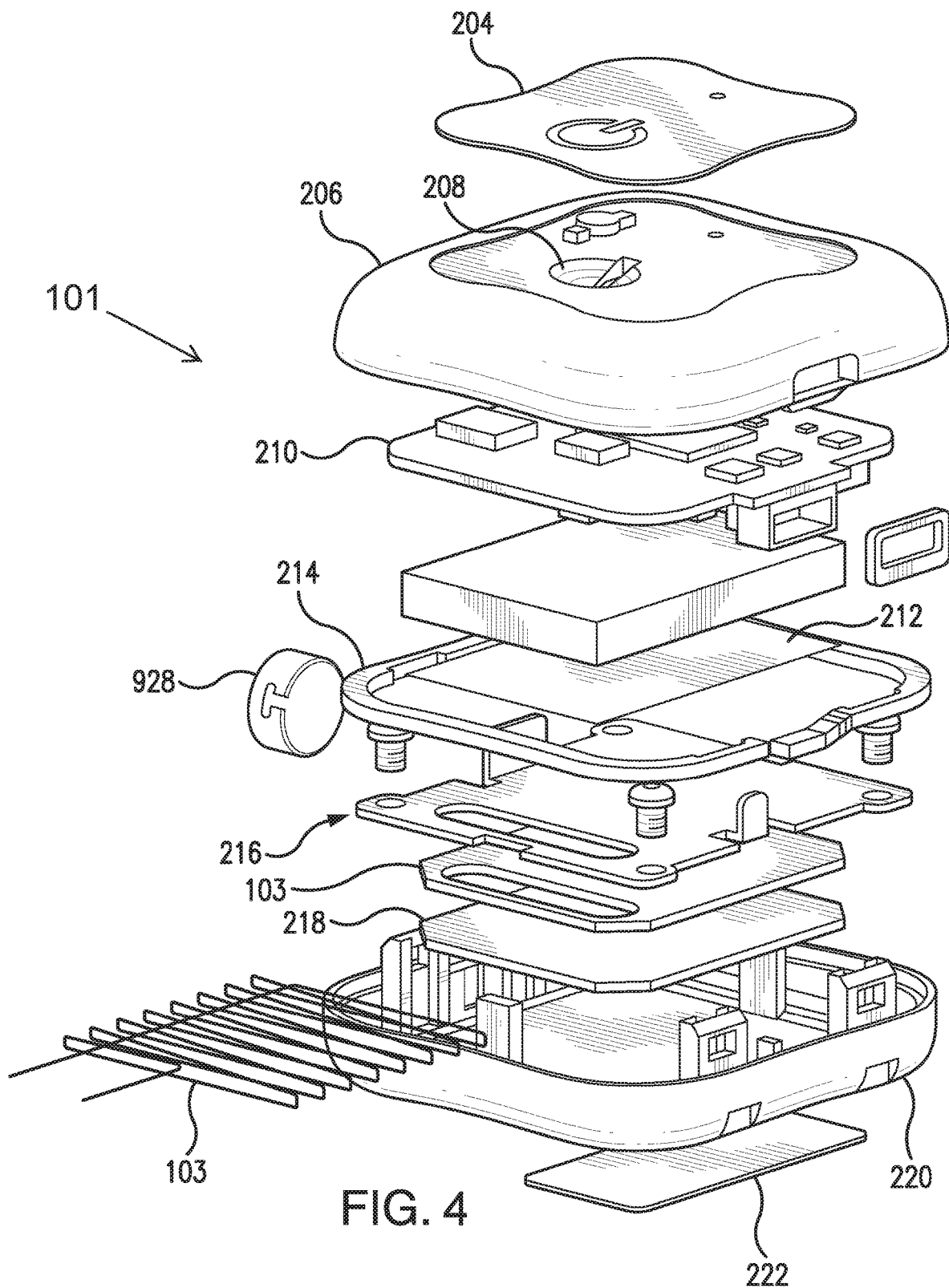
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
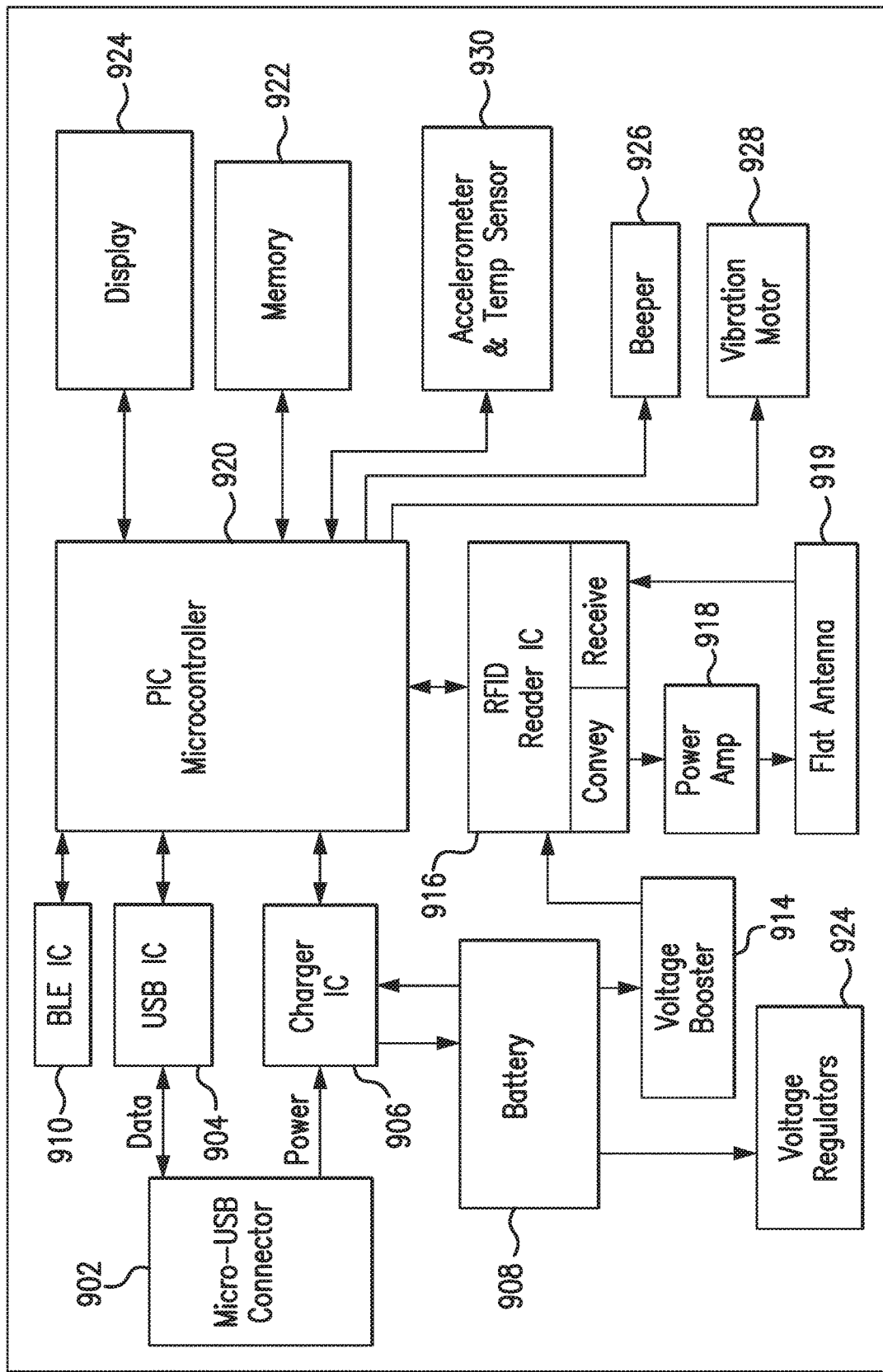
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 902. For example, in one alternative embodiment, the transceiver 101 may include a spring-based connector (e.g., Pogo pin connector) in addition to (or as an alternative to) Micro-USB connector 902, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 may receive raw signals indicative of an amount or concentration of an analyte in the interstitial fluid ("ISF") in proximity to the analyte indicator element 106 of the analyte sensor 100. In some embodiments, the transceiver 101 may receive the raw signals from the sensor 100 periodically (e.g., every 1, 2, 5, 10, 15, or 20 minutes). In some embodiments, the raw signals may include one or more measurements (e.g., one or more measurements indicative of the level of emission light 331 from the indicator molecules 104 as measured by the photodetector 224, one or more measurements indicative of the level of reference light 333 as measured by photodetector 226, and/or one or more temperature measurements as measured by the temperature transducer 670). In some embodiments, the transceiver 101 may use the received raw signals to calculate an ISF analyte level.

In some embodiments, the transceiver 101 may use the calculated ISF analyte level and one or more previously calculated ISF analyte levels to calculate a rate of change of the interstitial fluid analyte level ("ISF_ROC"). In some non-limiting embodiments, to calculate ISF_ROC, the transceiver 101 may use just the calculated ISF analyte level and the most recent previously calculated ISF analyte level and determine ISF_ROC as the difference between the calculated ISF analyte level and most recent previously calculated ISF analyte level divided by the time difference between a time stamp for the calculated ISF analyte level and a time stamp for the most recent previously calculated ISF analyte level. In some alternative embodiments, to calculate ISF_ROC, the transceiver 101 may use the calculated ISF analyte level and a plurality of the most recent previously calculated ISF analyte levels. In some non-limiting embodiments, the plurality of the most recent previously calculated ISF analyte levels may be, for example and without limitation, the previous two calculated ISF analyte levels, the previous 20 calculated ISF analyte levels, or any number of previously calculated ISF analyte levels in between (e.g., the previous 5 calculated analyte levels). In other alternative embodiments, to calculate ISF_ROC, the transceiver 101 may use the calculated ISF analyte level and the previously calculated ISF analyte levels that were calculated during a time period. In some non-limiting embodiments, the time period may be, for example and without limitation, the last one minute, the last 60 minutes, or any amount of time in between (e.g., the last 25 minutes). In some embodiments where the transceiver 101 uses the calculated ISF analyte level and more than one previously calculated ISF analyte levels to calculate ISF_ROC, the transceiver 101 may use, for example, linear or non-linear regression to calculate ISF_ROC.

In some embodiments, the transceiver 101 may convert the calculated ISF analyte level into a blood analyte level by performing a lag compensation, which compensates before the lag between blood analyte level and an ISF analyte level. In some embodiments, the transceiver 101 may calculate the blood analyte level using at least the calculated ISF analyte level and the calculated ISF_ROC. In some non-limiting embodiments, the transceiver 101 may calculate the blood analyte level as $ISF\_ROC/p_2+(1+p_3/p_2)*ISF\_analyte$, where $p_2$ is analyte diffusion rate, $p_3$ is the analyte consumption rate, and ISF_analyte is the calculated ISF analyte level.

In some embodiments, the transceiver 101 may store one or more of the calculated ISF analyte level, calculated ISF_ROC, and calculated blood analyte level (e.g., in memory 922). In some embodiments, the transceiver 101 may convey the calculated blood analyte level to the display device 105, and the display device 105 may display the calculated blood analyte level. However, for real-time display of blood analyte levels, only the current calculated ISF analyte level and one or more past ISF analyte levels can be used to estimate the ISF_ROC because subsequent/future ISF analyte levels are not yet available. Accordingly, in some embodiments, after one or more subsequent ISF analyte levels are calculated, the transceiver 101 may use the one or more subsequent ISF analyte levels to correct the calculated blood analyte level. That is, at a later time, both past and future ISF analyte values are available, and the transceiver 101 may use past and future ISF analyte values to update the ISF_ROC and calculate a corrected blood analyte value, which may be more accurate than the uncorrected, lag-compensated blood analyte value. In addition, corrected blood analyte values may be smoother than uncorrected, lag-compensated blood analyte values when shown over time.

In some embodiments, the transceiver 101 may calculate the updated ISF_ROC using one or more past ISF analyte values, the calculated ISF analyte value, and one or more subsequent ISF analyte values. In some non-limiting embodiments, the transceiver 101 may use, for example, linear or non-linear regression to calculate the updated ISF_ROC. In some embodiments, the transceiver 101 may calculate the corrected blood analyte value using the updated ISF_ROC instead of the original ISF_ROC. In some non-limiting embodiments, the transceiver 101 may calculate the corrected blood analyte value as $updated\_ISF\_ROC/p_2+(1+p_3/p_2)*ISF\_analyte$, where $p_2$ is analyte diffusion rate, $p_3$ is the analyte consumption rate, updated_ISF_ROC is the calculated updated ISF_ROC, and ISF_analyte is the calculated ISF analyte level.

In some embodiments, the transceiver 101 may store one or more of the updated ISF_ROC and the corrected blood analyte level (e.g., in memory 922). In some embodiments, the transceiver 101 may convey the corrected blood analyte level to the display device 105, and the display device 105 may display the corrected blood analyte level. In some embodiments, the display device may be configured to display an uncorrected, lag-compensated blood analyte value until the display device 105 receives the corrected blood analyte level and, after receiving the corrected blood analyte level, display the corrected blood analyte level instead of the uncorrected blood analyte level. In some embodiments, the display device 105 may be configured to display uncorrected, lag-compensated blood analyte value for real-time display. In some embodiments, the display device 105 may be configured to also display uncorrected, lag-compensated blood analyte value for historical blood analyte level display (e.g., a display of blood analyte levels over time) but only until the display device 105 receives the corrected blood analyte level.

Figure 6A:
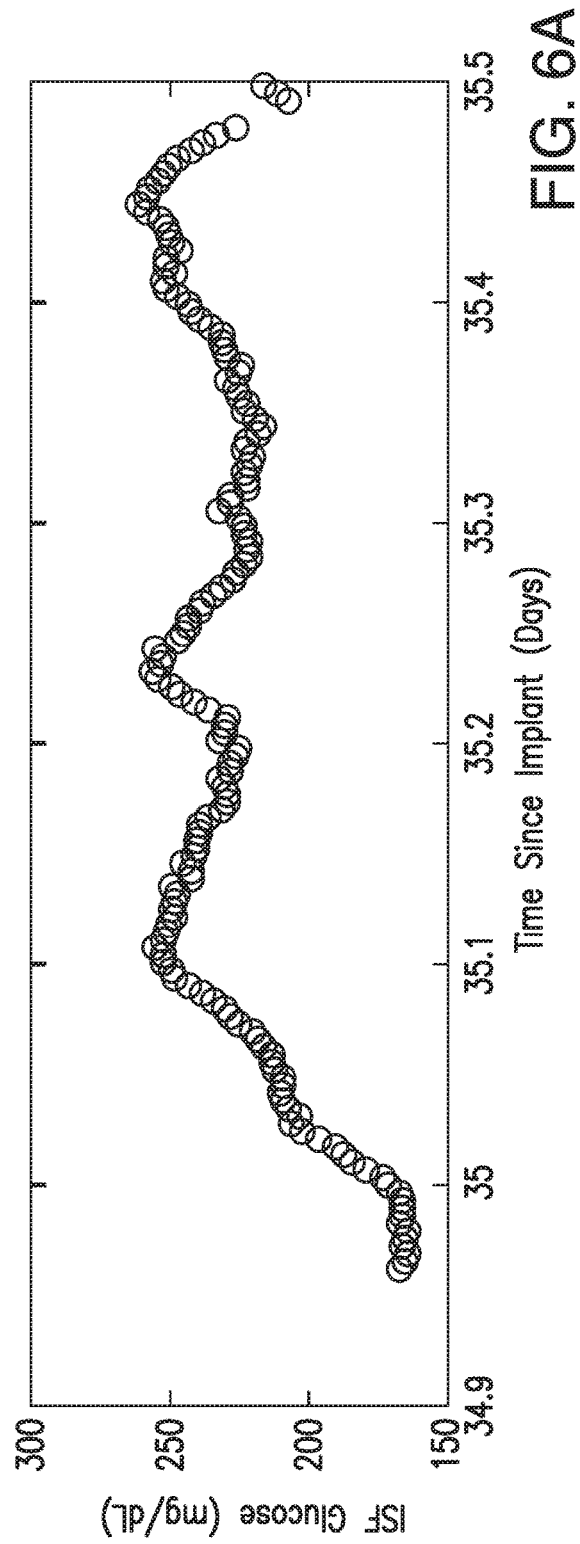
FIGS. 6A-6C show an example in which interstitial fluid glucose levels within time range from 15 minutes into the future to 25 minutes into the past are used to calculate updated rates of change of the interstitial fluid analyte level and correct blood glucose levels.
Figure 6B:
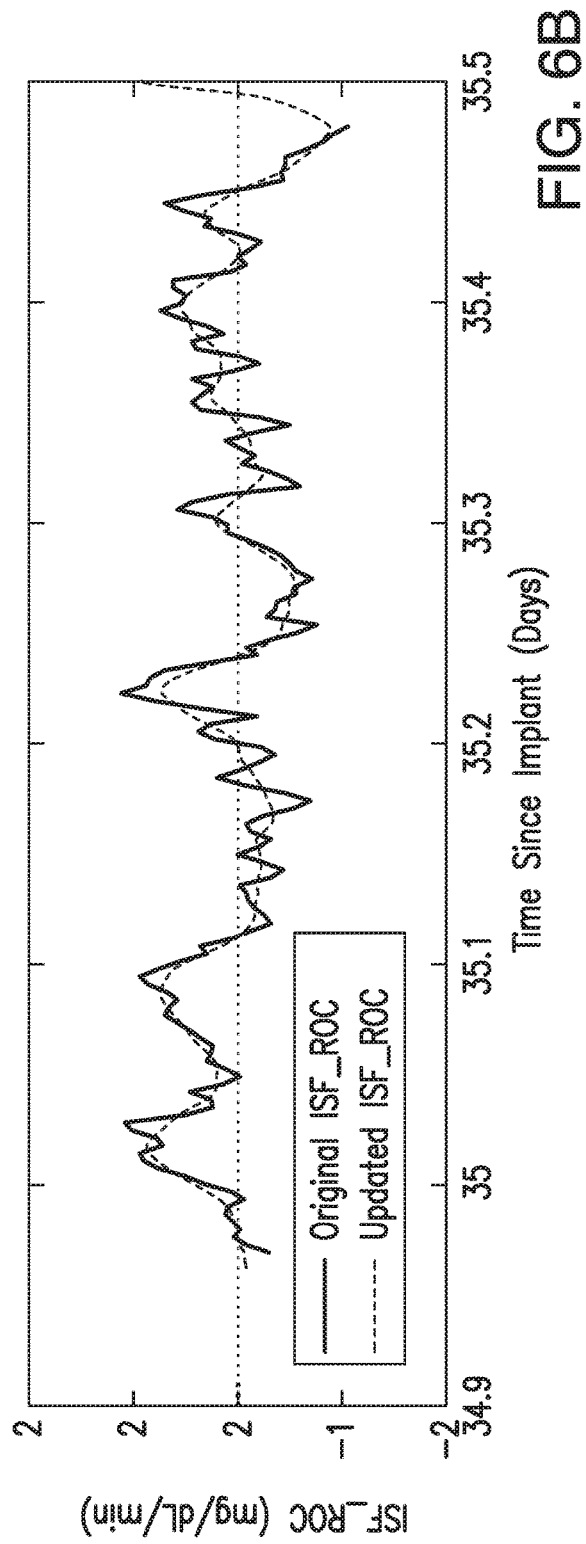
Figure 6C:
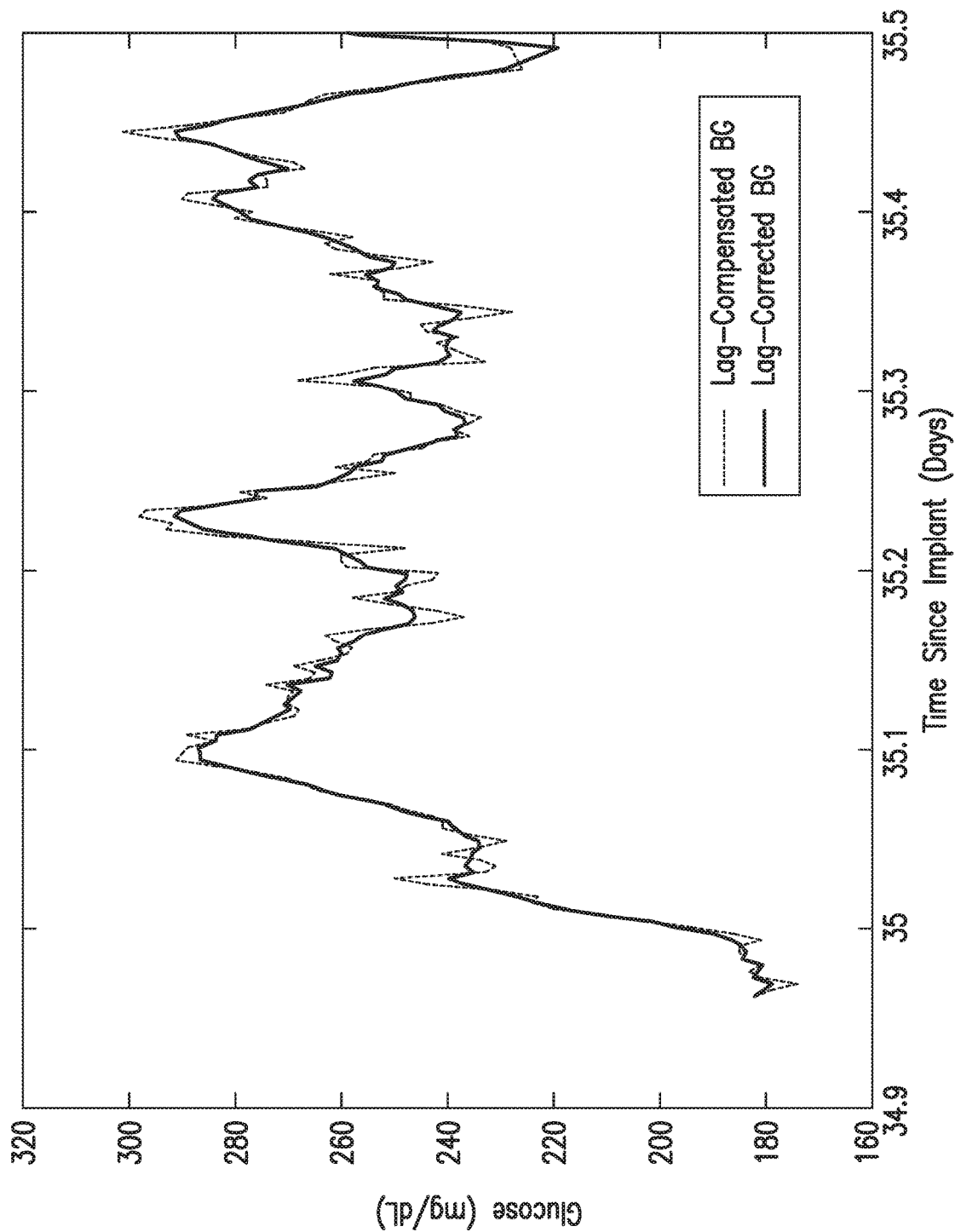

FIGS. 6A-6C show an example in which ISF glucose levels within time range from 15 minutes into the future to 25 minutes into the past are used to calculate updated ISF_ROC values and correct blood glucose ("BG") levels. FIG. 6A shows ISF glucose levels over time. FIG. 6B shows original and updated ISF_ROC values over time. FIG. 6C shows uncorrected, lag-compensated BG levels and lag-corrected BG levels over time. In the example illustrated in FIGS. 6A-6C, the transceiver 101 may (i) calculate an original ISF_ROC using an ISF glucose level and one or more ISF glucose levels in a 25-minute window into the past, (ii) calculate a lag-compensated BG level using the ISF glucose level, and (iii) convey the lag-compensated BG level to the display device 105 for real-time and historical BG display. Then, after a 15-minute delay, the transceiver 101 may (i) calculate an updated ISF_ROC using the ISF glucose level, the one or more ISF glucose levels in the 25-minute window into the past, and one or more ISF glucose levels during the 15-minute delay, (ii) calculate a corrected BG level using the ISF glucose level and the updated ISF_ROC, and (iii) convey the corrected BG level to the display device 105 to update the historical BG display. In the example illustrated in FIGS. 6A-6C, the sampling period for sensor measurement is 5 minutes. That is, the transceiver 101 receives sensor data from the analyte sensor 100 every 5 minutes, the 25-minute window into the past includes 5 previous ISF glucose measurements, and the 15-minute window into the future includes 3 subsequent measurements.

Figure 7:
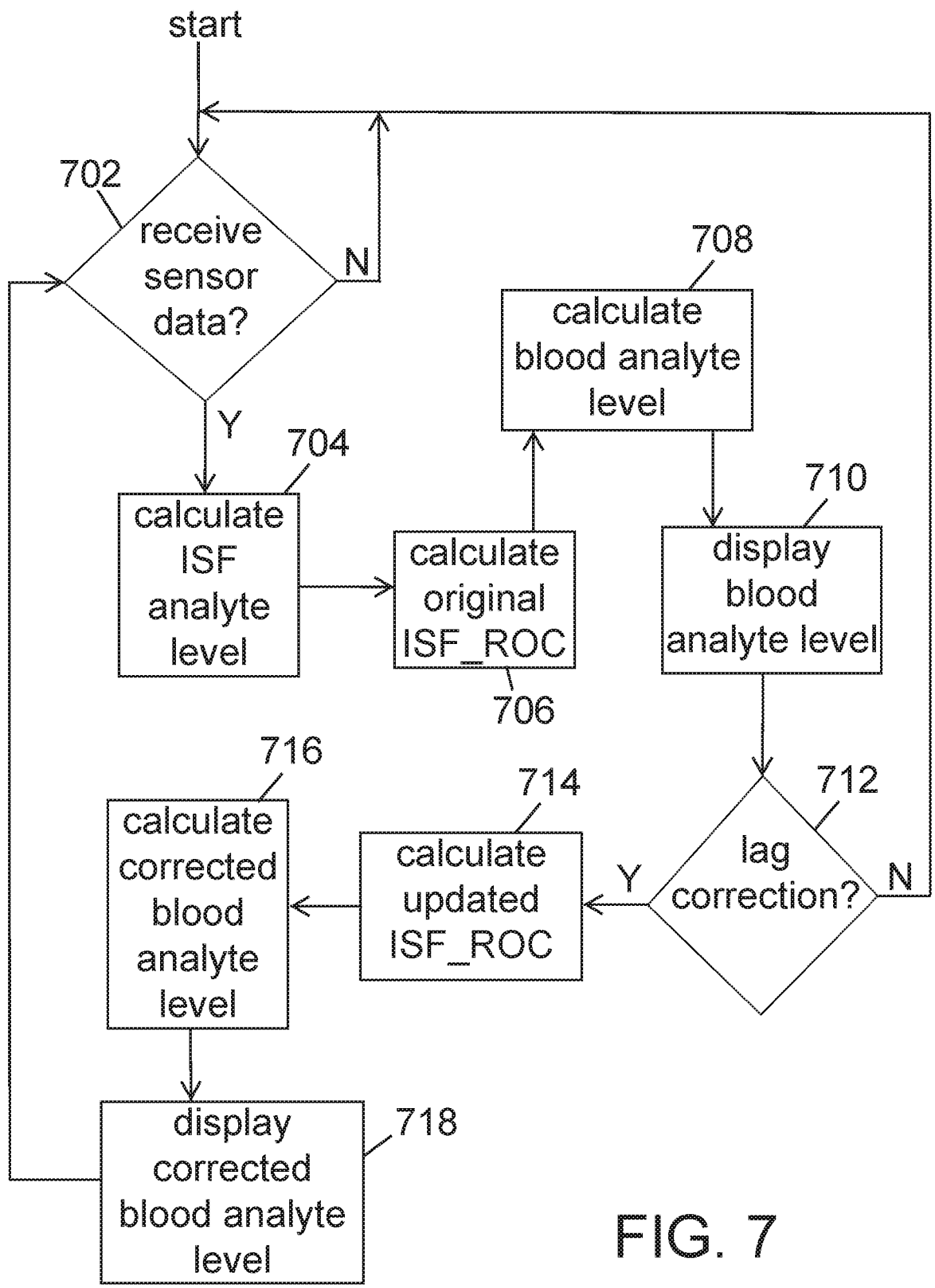
FIG. 7 is a flow chart illustrating an iterative process for calculating and correcting blood analyte levels.

FIG. 7 is a flow chart illustrating an iterative process 700 for calculating and correcting blood analyte levels. In some embodiments, one or more steps of the process 700 may be performed by an analyte monitoring system, such as, for example, the analyte monitoring system 50. In some embodiments, one or more steps of the process 700 may be performed by a transceiver, such as, for example, the transceiver 101. In some non-limiting embodiments, one or more steps of the process 700 may be performed by a processor, such as, for example, the PIC microcontroller 920 of the transceiver 101.

In some embodiments, the process 700 may include a step 702 in which the transceiver 101 determines whether the transceiver 101 has received sensor data from the sensor 100. In some embodiments, the sensor data may include one or more sensor measurements, such as, for example and without limitation, one or more light measurements and/or one or more temperature measurements. In some embodiments, the transceiver 101 may receive the sensor data after conveying a command (e.g., a measurement command or a read sensor data command) to the sensor 100. However, this is not required, and, in some alternative embodiments, the sensor 100 may control when sensor data is conveyed to the transceiver 101, or the sensor 100 may continuously convey sensor data to the transceiver 101. In some non-limiting embodiments, the transceiver 101 may receive the sensor data periodically (e.g., every 1, 2, 5, 10, or 15 minutes).

In some embodiments, the transceiver 101 may receive the sensor data wirelessly. For example and without limitation, in some non-limiting embodiments, the transceiver 101 may receive the sensor data by detecting modulations in an electromagnetic wave generated by the sensor 100, e.g., by detecting modulations in the current flowing through the coil 103 of the transceiver 101. However, this is not required, and, in some alternative embodiments, the transceiver 101 may receive the sensor data via a wired connection to the sensor 100.

In some embodiments, the sensor data may be associated with a time stamp. In some non-limiting embodiments, the transceiver 101 may receive the time stamp from the sensor 100. In some non-limiting embodiments, the received sensor data may include the time stamp. In some embodiments, the time stamp may reflect the time at which one or more sensor measurements included in the sensor data were taken. However, it is not required that the transceiver 101 receive the time stamp from the sensor 100. For example, in some alternative embodiments, the transceiver 101 may assign the time stamp to the sensor data after receiving the sensor data. In these embodiments, the time stamp may reflect when the transceiver 101 received the sensor data.

In some non-limiting embodiments, if the sensor 100 has received sensor data, the process 700 may proceed from step 702 to an ISF analyte level calculation step 704. In some non-limiting embodiments, if the transceiver 101 has not received sensor data, the process 700 may return to step 702.

In some non-limiting embodiments, the process 700 may include the step 704 in which the transceiver 101 calculates an ISF analyte level using the received sensor data. In some embodiments, the ISF analyte level may be a measurement of the amount or concentration of the analyte in the interstitial fluid in proximity to the analyte indicator element 106. In some non-limiting embodiments, calculation of the ISF analyte level may include, for example and without limitation, some or all of the features described in U.S. application Ser. No. 13/937,871, filed on Jul. 9, 2013, which is incorporated by reference herein in its entirety.

In some non-limiting embodiments, the process 700 may include a step 706 in which the transceiver 101 calculates ISF_ROC. In some embodiments, the transceiver 101 may calculate the ISF_ROC using at least the calculated ISF analyte level and one or more previously calculated ISF analyte levels (e.g., one or more ISF analyte levels calculated using previously received sensor data). In some non-limiting embodiments, the process 700 may include a step 708 in which the transceiver 101 calculates a blood analyte level. In some embodiments, the transceiver 101 may calculate the blood analyte level by performing a lag compensation. In some embodiments, the transceiver 101 may calculate the blood analyte level using at least the ISF analyte level and the ISF_ROC calculated in steps 704 and 706, respectively.

In some non-limiting embodiments, the process 700 may include a step 710 of displaying the calculated blood analyte level. In some embodiments, the step 710 may include displaying the calculated blood analyte level on a display (e.g., display 924) of the transceiver 101. In some embodiments, the step 710 may additionally or alternatively include the transceiver 101 conveying the calculated blood analyte level to a display device (e.g., display device 105) for display. In some non-limiting embodiments, the transceiver 101 may convey the calculated blood analyte level to the display device 105 via wired or wireless communication using the connector IC 904 or wireless communication IC 910. In some embodiments, the display device 105 may be configured to receive and display the conveyed blood analyte level. In some non-limiting embodiments, the display device 105 may display the received blood analyte level as a current blood analyte level (e.g., until a subsequent blood analyte level is received) and then as a historical/previous blood analyte level.

In some non-limiting embodiments, the process 700 may include a step 712 in which the transceiver 101 determines whether to perform a lag correction for one or more previously calculated blood analyte levels (i.e., one or more lag-compensated but uncorrected blood analyte levels). In some non-limiting embodiments, the transceiver 101 may determine to lag-correct an uncorrected, lag-compensated blood analyte value if a threshold amount of time has passed since the blood analyte value was calculated. In some non-limiting embodiments, the threshold amount of time may be, for example and without limitation, 1 minute, 60 minutes, or any amount of time in between (e.g., 25 minutes). In some non-limiting alternative embodiments, the transceiver 101 may determine to lag-correct an uncorrected, lag-compensated blood analyte value if a threshold amount of ISF analyte levels have been calculated since the blood analyte level was calculated. In some non-limiting embodiments, the threshold of amount of ISF analyte levels calculated since the blood analyte level was calculated may be an integer in the range from 1 to 20. In some embodiments, if the transceiver 101 determines to perform a lag correction, the process 700 may proceed to an ISF_ROC updating step 714. In some embodiments, if the transceiver 101 determines not to perform a lag correction, the process 700 may proceed back to step 702.

However, the step 712 of determining whether to perform a lag correction is not required. For example, in some alternative embodiments, the transceiver 101 may perform a lag correction for one or more uncorrected, lag-compensated blood analyte levels automatically each time a new ISF analyte level is calculated.

In some non-limiting embodiments, the process 700 may include the ISF_ROC updating step 714. In some embodiments, the ISF_ROC updating step 714 may include the transceiver 101 calculating an updated ISF_ROC for lag correcting a lag-compensated blood analyte level. The lag-compensated blood analyte level may have been calculated using a first ISF analyte level and an original ISF_ROC. In some non-limiting embodiments, the transceiver 101 may calculate an updated ISF_ROC using (i) one or more past ISF analyte values (e.g., one or more ISF analyte values having time stamps prior to the time stamp of the first ISF analyte level), (ii) the first ISF analyte level, and (iii) one or more subsequent ISF analyte values (e.g., one or more ISF analyte values having time stamps later than the time stamp of the first ISF analyte level).

In some non-limiting embodiments, the process 700 may include a step 716 in which the transceiver 101 calculates a corrected blood analyte level. In some embodiments, the transceiver 101 may calculate the corrected blood analyte value using the updated ISF_ROC instead of the original ISF_ROC. In some non-limiting embodiments, the transceiver 101 may calculate the corrected blood analyte value using at least the updated ISF_ROC and the first ISF analyte level.

In some non-limiting embodiments, the process 700 may include a step 718 of displaying the corrected blood analyte level. In some embodiments, the step 718 may include displaying the calculated blood analyte level on a display (e.g., display 924) of the transceiver 101. In some embodiments, the step 718 may additionally or alternatively include the transceiver 101 conveying the corrected blood analyte level to a display device (e.g., display device 105) for display. In some non-limiting embodiments, the transceiver 101 may convey the corrected blood analyte level to the display device 105 via wired or wireless communication using the connector IC 904 or wireless communication IC 910. In some embodiments, the display device 105 may be configured to receive and display the corrected blood analyte level. In some non-limiting embodiments, the display device 105 may be configured to (i) display the uncorrected, lag-compensated blood analyte level until the display device 105 receives the corrected blood analyte level and (ii) after receiving the corrected blood analyte level, display the corrected blood analyte level instead of the uncorrected blood analyte level. In some embodiments, the process 700 may proceed from step 718 back to step 702.

In some embodiments, the steps of process 700 illustrated in FIG. 7 may be carried out in the order illustrated in FIG. 7. However, this is not required. For example, in some alternative embodiments, steps 712-718 may be performed any time after step 704 (e.g., in between steps 704 and 706, in between steps 706 and 708, in between steps 708 and 710, and/or simultaneously or interspersed with steps 706-710) and need not be performed after step 710. In some alternative embodiments, steps 710 and 718 may be performed simultaneously.

Figure 8:
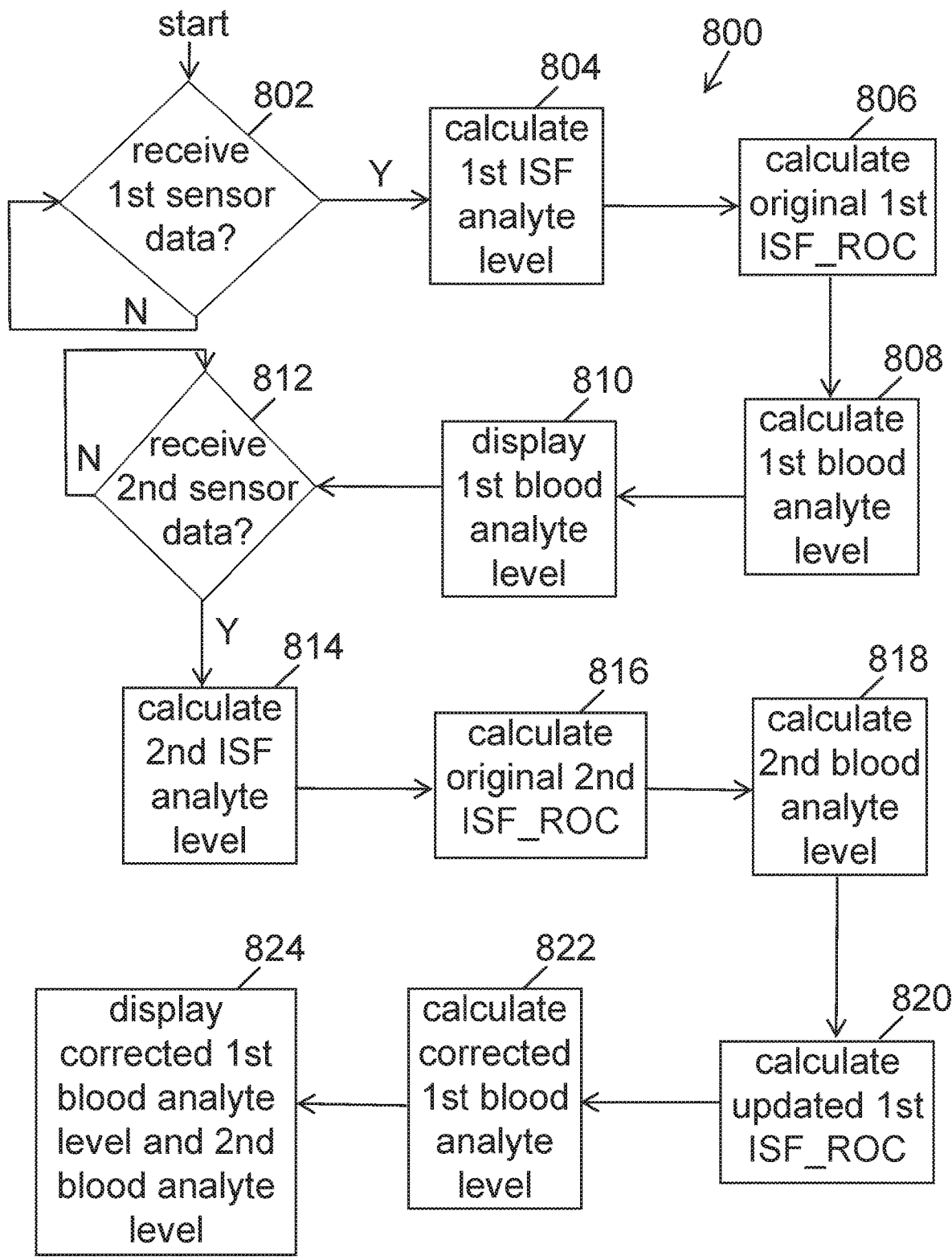
FIG. 8 is a flow chart illustrating a process for calculating and correcting blood analyte levels.

FIG. 8 is a flow chart illustrating a process 800 for calculating and correcting blood analyte levels. In some embodiments, the process 800 may be a non-limiting example of steps performed by the iterative process 700 illustrated in FIG. 7. In some embodiments, one or more steps of the process 800 may be performed by an analyte monitoring system, such as, for example, the analyte monitoring system 50. In some embodiments, one or more steps of the process 800 may be performed by a transceiver, such as, for example, the transceiver 101. In some non-limiting embodiments, one or more steps of the process 800 may be performed by a processor, such as, for example, the PIC microcontroller 920 of the transceiver 101.

In some embodiments, the process 800 may include a step 802 in which the transceiver 101 determines whether the transceiver 101 has received first sensor data from the sensor 100. In some embodiments, the first sensor data may include a set of one or more sensor measurements, such as, for example and without limitation, one or more light measurements and/or one or more temperature measurements.

In some embodiments, the first sensor data may be associated with a first time stamp. In some non-limiting embodiments, the transceiver 101 may receive the first time stamp from the sensor 100. In some non-limiting embodiments, the received first sensor data may include the first time stamp. In some embodiments, the first time stamp may reflect the time at which one or more sensor measurements included in the first sensor data were taken. However, it is not required that the transceiver 101 receive the first time stamp from the sensor 100. For example, in some alternative embodiments, the transceiver 101 may assign the first time stamp to the first sensor data after receiving the first sensor data. In these embodiments, the first time stamp may reflect when the transceiver 101 received the first sensor data.

In some non-limiting embodiments, if the sensor 100 has received first sensor data, the process 800 may proceed from step 802 to a first ISF analyte level calculation step 804. In some non-limiting embodiments, if the transceiver 101 has not received first sensor data, the process 800 may return to step 802.

In some non-limiting embodiments, the process 800 may include the step 804 in which the transceiver 101 calculates a first ISF analyte level using the received first sensor data. In some embodiments, the first ISF analyte level may be a measurement of the amount or concentration of the analyte in the interstitial fluid in proximity to the analyte indicator element 106. In some non-limiting embodiments, the process 800 may include a step 806 in which the transceiver 101 calculates a first ISF_ROC. In some embodiments, the transceiver 101 may calculate the first ISF_ROC using at least the calculated first ISF analyte level and one or more previously calculated ISF analyte levels (e.g., one or more ISF analyte levels calculated using previously received sensor data). In some non-limiting embodiments, the process 800 may include a step 808 in which the transceiver 101 calculates a first blood analyte level. In some embodiments, the transceiver 101 may calculate the first blood analyte level by performing a lag compensation. In some embodiments, the transceiver 101 may calculate the first blood analyte level using at least the first ISF analyte level and the first ISF_ROC calculated in steps 804 and 806, respectively.

In some non-limiting embodiments, the process 800 may include a step 810 of displaying the calculated first blood analyte level. In some embodiments, the step 810 may include displaying the calculated first blood analyte level on a display (e.g., display 924) of the transceiver 101. In some embodiments, the step 810 may additionally or alternatively include the transceiver 101 conveying the calculated first blood analyte level to a display device (e.g., display device 105) for display. In some non-limiting embodiments, the transceiver 101 may convey the calculated first blood analyte level to the display device 105 via wired or wireless communication using the connector IC 904 or wireless communication IC 910. In some embodiments, the display device 105 may be configured to receive and display the conveyed first blood analyte level. In some non-limiting embodiments, the display device 105 may display the first blood analyte level as a current blood analyte level (e.g., until a subsequent blood analyte level is received) and then as a historical/previous blood analyte level.

In some embodiments, the process 800 may include a step 812 in which the transceiver 101 determines whether the transceiver 101 has received second sensor data from the sensor 100. In some embodiments, the second sensor data may include a second set of one or more sensor measurements, such as, for example and without limitation, one or more light measurements and/or one or more temperature measurements.

In some embodiments, the second sensor data may be associated with a second time stamp. In some embodiments, the time recorded by the second time stamp may be later than the time recorded by the first time stamp. In some non-limiting embodiments, the transceiver 101 may receive the second time stamp from the sensor 100. In some non-limiting embodiments, the received second sensor data may include the second time stamp. In some embodiments, the second time stamp may reflect the time at which one or more sensor measurements included in the second sensor data were taken. However, it is not required that the transceiver 101 receive the second time stamp from the sensor 100. For example, in some alternative embodiments, the transceiver 101 may assign the second time stamp to the second sensor data after receiving the second sensor data. In these embodiments, the second time stamp may reflect when the transceiver 101 received the second sensor data.

In some non-limiting embodiments, if the sensor 100 has received second sensor data, the process 800 may proceed from step 812 to a second ISF analyte level calculation step 814. In some non-limiting embodiments, if the transceiver 101 has not received second sensor data, the process 800 may return to step 812.

In some non-limiting embodiments, the process 800 may include the step 814 in which the transceiver 101 calculates a second ISF analyte level using the received second sensor data. In some embodiments, the second ISF analyte level may be a measurement of the amount or concentration of the analyte in the interstitial fluid in proximity to the analyte indicator element 106.

In some non-limiting embodiments, the process 800 may include a step 816 in which the transceiver 101 calculates a second ISF_ROC. In some embodiments, the transceiver 101 may calculate the second ISF_ROC using at least the calculated second ISF analyte level and one or more previously calculated ISF analyte levels (e.g., one or more ISF analyte levels calculated using previously received sensor data, such as, for example and without limitation, the first ISF analyte level calculated in step 804). In some non-limiting embodiments, the process 800 may include a step 818 in which the transceiver 101 calculates a second blood analyte level. In some embodiments, the transceiver 101 may calculate the second blood analyte level by performing a lag compensation. In some embodiments, the transceiver 101 may calculate the second blood analyte level using at least the second ISF analyte level and the second ISF_ROC calculated in steps 814 and 816, respectively.

In some non-limiting embodiments, the process 800 may include a step 820 in which the transceiver 101 calculates an updated first ISF_ROC for lag correcting the lag-compensated, first blood analyte level. The first blood analyte level may have been calculated using the first ISF analyte level and the original first ISF_ROC. In some non-limiting embodiments, the transceiver 101 may calculate the updated first ISF_ROC using (i) one or more past ISF analyte values (e.g., one or more ISF analyte values having time stamps prior to the first time stamp of the first ISF analyte level), (ii) the first ISF analyte level, and (iii) one or more subsequent ISF analyte values (e.g., one or more ISF analyte values having a time stamp later than the time stamp of the first ISF analyte level, such as, for example and without limitation, the second ISF analyte level).

In some non-limiting embodiments, the process 800 may include a step 822 in which the transceiver 101 calculates a corrected first blood analyte level. In some embodiments, the transceiver 101 may calculate the corrected first blood analyte value using the updated first ISF_ROC instead of the original first ISF_ROC. In some non-limiting embodiments, the transceiver 101 may calculate the corrected first blood analyte value using at least the updated first ISF_ROC and the first ISF analyte level.

In some non-limiting embodiments, the process 800 may include a step 824 of displaying one or more of the second blood analyte level and the corrected first blood analyte level. In some embodiments, the step 824 may include displaying one or more of the calculated second blood analyte level and the corrected first blood analyte level on a display (e.g., display 924) of the transceiver 101. In some embodiments, the step 824 may additionally or alternatively include the transceiver 101 conveying one or more of the second blood analyte level and the corrected first blood analyte level to a display device (e.g., display device 105) for display. In some non-limiting embodiments, the transceiver 101 may convey one or more of the second blood analyte level and the corrected first blood analyte level to the display device 105 via wired or wireless communication using the connector IC 904 or wireless communication IC 910. In some embodiments, the display device 105 may be configured to receive and display one or more of the second blood analyte level and the corrected first blood analyte level. In some non-limiting embodiments, the display device 105 may be configured to (i) display the uncorrected, lag-compensated first blood analyte level until the display device 105 receives the corrected first blood analyte level and (ii) after receiving the corrected first blood analyte level, display the corrected first blood analyte level instead of the uncorrected first blood analyte level. In some non-limiting embodiments, the display device 105 may display the second blood analyte level as a current blood analyte level and may display the corrected first blood analyte level instead of the uncorrected first blood analyte level as a historical/previous blood analyte level.

In some embodiments, the steps of process 800 illustrated in FIG. 8 may be carried out in the order illustrated in FIG. 8. However, this is not required. For example, in some alternative embodiments, steps 820 and 822 may be performed before steps 816 and 818, simultaneously with steps 816 and 818, or interspersed with steps 816 and 818 (e.g., performed in the order of steps 820, 816, 822, 818; steps 816, 820, 822, 818; steps 820, 816, 818, 822; steps 816, 820, 818, 822). In some alternative embodiments, step 824 may be broken into separate steps of displaying the second blood analyte level and displaying the corrected first blood analyte level, which may be performed after steps 818 and 822, respectively.

In some embodiments, steps 820 and 822 may be performed only after the transceiver 101 determines that a lag correction should be performed for the lag-compensated but uncorrected first blood analyte level calculated in step 808. For example and without limitation, in some non-limiting embodiments, the transceiver 101 may determine to lag-correct the uncorrected, lag-compensated first blood analyte value if a threshold amount of time (e.g., T minutes, where $1 \leq T \leq 60$) has passed since the first blood analyte value was calculated and/or if a threshold amount of ISF analyte levels have been calculated since the first blood analyte level was calculated. However, a step of determining whether to perform a lag correction for the uncorrected, lag-compensated first blood analyte value is not required. For example, in some alternative embodiments, the transceiver 101 may perform a lag correction for the uncorrected, lag-compensated first blood analyte levels automatically following calculation of the second ISF analyte level in step 814.

Figure 9:
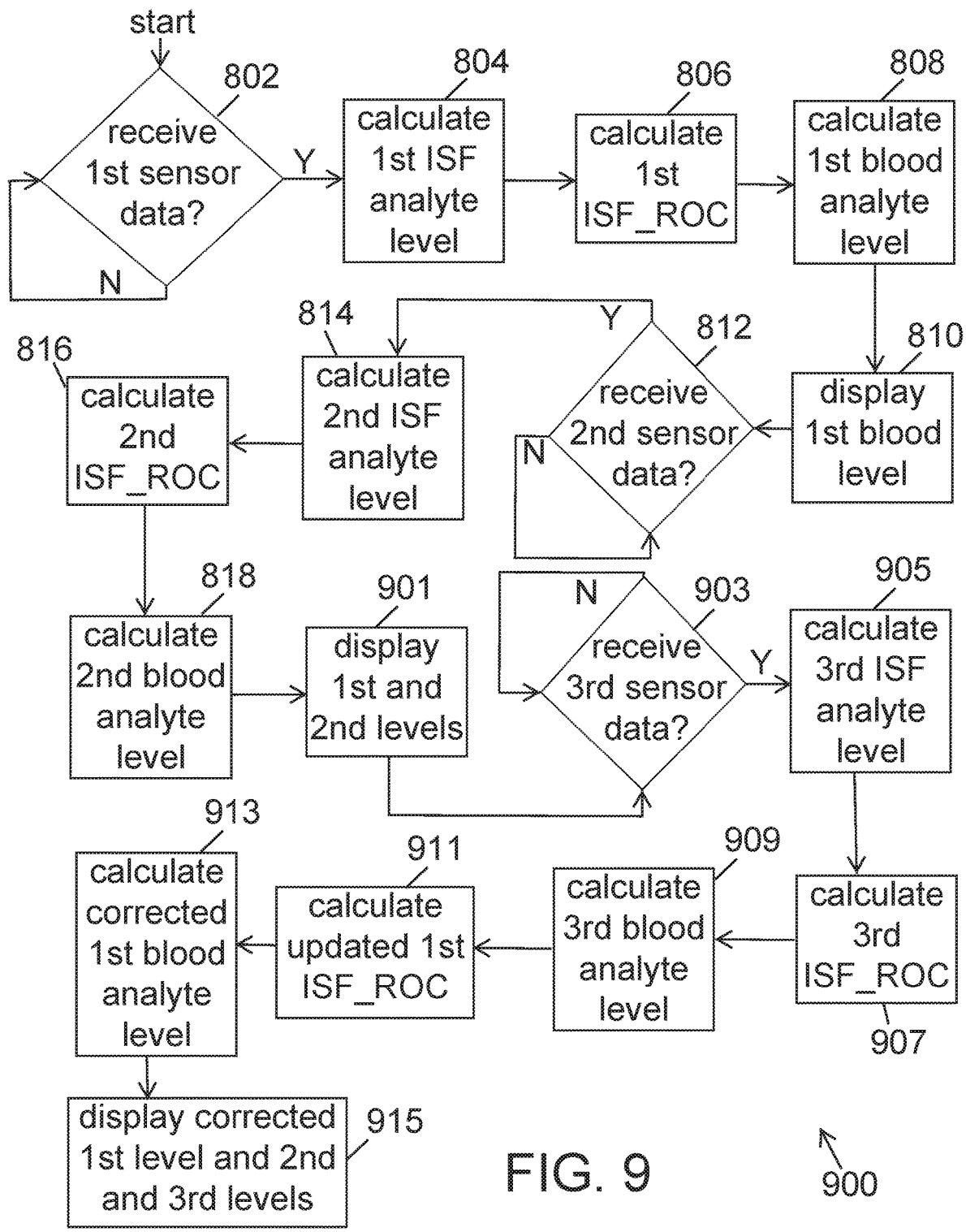
FIG. 9 is a flow chart illustrating a process for calculating and correcting blood analyte levels.

FIG. 9 is a flow chart illustrating a process 900 for calculating and correcting blood analyte levels. In some embodiments, the process 900 may be a non-limiting example of steps performed by the iterative process 700 illustrated in FIG. 7. In some embodiments, one or more steps of the process 900 may be performed by an analyte monitoring system, such as, for example, the analyte monitoring system 50. In some embodiments, one or more steps of the process 900 may be performed by a transceiver, such as, for example, the transceiver 101. In some non-limiting embodiments, one or more steps of the process 900 may be performed by a processor, such as, for example, the PIC microcontroller 920 of the transceiver 101.

In some embodiments, the process 900 may include one or more of steps 802, 804, 806, 808, 810, 812, 814, 816, and 818, which may be the same as the corresponding steps of process 800. In some embodiments, the process 900 may include a step 901 of displaying one or more of the first and second blood analyte levels calculated in steps 808 and 818, respectively. In some embodiments, the step 901 may include displaying one or more of the calculated first and second blood analyte levels on a display (e.g., display 924) of the transceiver 101. In some embodiments, the step 901 may additionally or alternatively include the transceiver 101 conveying one or more of the first and second blood analyte levels to a display device (e.g., display device 105) for display. In some non-limiting embodiments, the transceiver 101 may convey one or more of the first and second blood analyte levels to the display device 105 via wired or wireless communication using the connector IC 904 or wireless communication IC 910. In some embodiments, the display device 105 may be configured to receive and display one or more of the first and second blood analyte levels. In some non-limiting embodiments, the display device 105 may display the second blood analyte level as a current blood analyte level and may display the corrected first blood analyte level instead of the uncorrected first blood analyte level as a historical/previous blood analyte level.

In some embodiments, the process 800 may include a step 903 in which the transceiver 101 determines whether the transceiver 101 has received third sensor data from the sensor 100. In some embodiments, the third sensor data may include a third set of one or more sensor measurements, such as, for example and without limitation, one or more light measurements and/or one or more temperature measurements.

In some embodiments, the third sensor data may be associated with a third time stamp. In some embodiments, the time recorded by the third time stamp may be later than the time recorded by the second time stamp. In some non-limiting embodiments, the transceiver 101 may receive the third time stamp from the sensor 100. In some non-limiting embodiments, the received third sensor data may include the third time stamp. In some embodiments, the third time stamp may reflect the time at which one or more sensor measurements included in the third sensor data were taken. However, it is not required that the transceiver 101 receive the third time stamp from the sensor 100. For example, in some alternative embodiments, the transceiver 101 may assign the third time stamp to the third sensor data after receiving the third sensor data. In these embodiments, the third time stamp may reflect when the transceiver 101 received the third sensor data.

In some non-limiting embodiments, if the sensor 100 has received third sensor data, the process 900 may proceed from step 903 to a third ISF analyte level calculation step 905. In some non-limiting embodiments, if the transceiver 101 has not received third sensor data, the process 900 may return to step 903.

In some non-limiting embodiments, the process 900 may include the step 905 in which the transceiver 101 calculates a third ISF analyte level using the received third sensor data. In some embodiments, the third ISF analyte level may be a measurement of the amount or concentration of the analyte in the interstitial fluid in proximity to the analyte indicator element 106.

In some non-limiting embodiments, the process 900 may include a step 907 in which the transceiver 101 calculates a third ISF_ROC. In some embodiments, the transceiver 101 may calculate the third ISF_ROC using at least the calculated third ISF analyte level and one or more previously calculated ISF analyte levels (e.g., one or more ISF analyte levels calculated using previously received sensor data, such as, for example and without limitation, one or more of the first and second ISF analyte levels calculated in steps 804 and 905, respectively). In some non-limiting embodiments, the process 900 may include a step 909 in which the transceiver 101 calculates a third blood analyte level. In some embodiments, the transceiver 101 may calculate the third blood analyte level by performing a lag compensation. In some embodiments, the transceiver 101 may calculate the third blood analyte level using at least the third ISF analyte level and the third ISF_ROC calculated in steps 905 and 907, respectively.

In some non-limiting embodiments, the process 900 may include a step 911 in which the transceiver 101 calculates an updated first ISF_ROC for lag correcting the lag-compensated, first blood analyte level. The first blood analyte level may have been calculated using the first ISF analyte level and the original first ISF_ROC. In some non-limiting embodiments, the transceiver 101 may calculate the updated first ISF_ROC using (i) one or more past ISF analyte values (e.g., one or more ISF analyte values having time stamps prior to the first time stamp of the first ISF analyte level), (ii) the first ISF analyte level, and (iii) one or more subsequent ISF analyte values (e.g., one or more ISF analyte values having a time stamp later than the time stamp of the first ISF analyte level, such as, for example and without limitation, one or more of the second and third ISF analyte levels).

In some non-limiting embodiments, the process 900 may include a step 913 in which the transceiver 101 calculates a corrected first blood analyte level. In some embodiments, the transceiver 101 may calculate the corrected first blood analyte value using the updated first ISF_ROC instead of the original first ISF_ROC. In some non-limiting embodiments, the transceiver 101 may calculate the corrected first blood analyte value using at least the updated first ISF_ROC and the first ISF analyte level calculated in steps 911 and 808, respectively.

In some non-limiting embodiments, the process 900 may include a step 915 of displaying one or more of the second blood analyte level, the third blood analyte levels, and the corrected first blood analyte level. In some embodiments, the step 915 may include displaying one or more of the second blood analyte level, the third blood analyte levels, and the corrected first blood analyte level on a display (e.g., display 924) of the transceiver 101. In some embodiments, the step 915 may additionally or alternatively include the transceiver 101 conveying one or more of the second blood analyte level, the third blood analyte levels, and the corrected first blood analyte level to a display device (e.g., display device 105) for display. In some non-limiting embodiments, the transceiver 101 may convey one or more of the second blood analyte level, the third blood analyte levels, and the corrected first blood analyte level to the display device 105 via wired or wireless communication using the connector IC 904 or wireless communication IC 910. In some embodiments, the display device 105 may be configured to receive and display one or more of the second blood analyte level, the third blood analyte levels, and the corrected first blood analyte level. In some non-limiting embodiments, the display device 105 may be configured to (i) display the uncorrected, lag-compensated first blood analyte level until the display device 105 receives the corrected first blood analyte level and (ii) after receiving the corrected first blood analyte level, display the corrected first blood analyte level instead of the uncorrected first blood analyte level. In some non-limiting embodiments, the display device 105 may display the third blood analyte level as a current blood analyte level, may display the second blood analyte level as a historical/previous blood analyte level, and may display the corrected first blood analyte level instead of the uncorrected first blood analyte level as a historical/previous blood analyte level. That is, the corrected first blood analyte level may replace the uncorrected first blood analyte level in a display of historical/previous blood analyte levels.

In some embodiments, the steps of process 900 illustrated in FIG. 9 may be carried out in the order illustrated in FIG. 9. However, this is not required. For example, in some alternative embodiments, steps 911 and 913 may be performed before steps 907 and 909, simultaneously with steps 907 and 909, or interspersed with steps 907 and 909 (e.g., performed in the order of steps 911, 907, 913, 909; steps 907, 911, 913, 909; steps 911, 907, 909, 913; steps 907, 911, 909, 913). In some alternative embodiments, step 915 may be broken into separate steps of displaying the third blood analyte level and displaying the corrected first blood analyte level, which may be performed after steps 909 and 913, respectively.

In some embodiments, steps 911 and 913 may be performed only after the transceiver 101 determines that a lag correction should be performed for the lag-compensated but uncorrected first blood analyte level calculated in step 808. For example and without limitation, in some non-limiting embodiments, the transceiver 101 may determine to lag-correct the uncorrected, lag-compensated first blood analyte value if a threshold amount of time (e.g., T minutes, where $1 \leq T \leq 60$) has passed since the first blood analyte value was calculated and/or if a threshold amount of ISF analyte levels have been calculated since the first blood analyte level was calculated. However, a step of determining whether to perform a lag correction for the uncorrected, lag-compensated first blood analyte value is not required. For example, in some alternative embodiments, the transceiver 101 may perform a lag correction for the uncorrected, lag-compensated first blood analyte levels automatically following calculation of the third ISF analyte level in step 905.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although FIG. 9 shows the process 900 calculating an updated first ISC_ROC and a corrected first blood analyte level in steps 911 and 913, respectively, after calculating two subsequent ISF analyte levels (i.e., are second and third ISF analyte levels), this is not required, and, in some alternative embodiments, the transceiver 101 may calculate more than two subsequent ISF analyte levels (e.g., N subsequent ISF analyte levels, where N is an integer in the range from 1 to 20).

In addition, although the invention is described above in the context of an analyte monitoring system that calculates blood analyte levels indirectly using measurements of analyte levels in interstitial fluid, the invention is applicable to any monitoring system that calculates levels in a first medium using measurements of levels in a second medium.

What is claimed is:

1. An analyte monitoring system comprising:
    an analyte sensor including an indicator element that exhibits one or more detectable properties based on an amount or concentration of an analyte in proximity to the indicator element; and
    a transceiver configured to:
        receive first sensor data from the analyte sensor;
        calculate a first interstitial fluid analyte level using at least the first sensor data;
        calculate a first interstitial fluid analyte level rate of change using at least the first interstitial fluid analyte level and one or more past interstitial fluid analyte levels;
        calculate a first blood analyte level using at least the first interstitial fluid analyte level and the first interstitial fluid analyte level rate of change;
        after receiving the first sensor data, receive second sensor data from the analyte sensor;
        calculate a second interstitial fluid analyte level using at least the second sensor data;
        calculate an updated first interstitial fluid analyte level rate of change using at least the first interstitial fluid analyte level, the second interstitial fluid analyte level, and the one or more past interstitial fluid analyte levels; and
        calculate a corrected first blood analyte level using at least the first interstitial fluid analyte level and the first interstitial fluid analyte level rate of change.

2. The system of claim 1, wherein the transceiver is further configured to:
    calculate a second interstitial fluid analyte level rate of change using at least the first and second interstitial fluid analyte levels; and
    calculate a second blood analyte level using at least the second interstitial fluid analyte level and the second interstitial fluid analyte level rate of change.

3. The system of claim 2, further comprising a display device configured to:
    receive and display the first blood analyte level;
    receive and display the second blood analyte level; and
    receive and display the corrected first blood analyte level.

4. The system of claim 1, further comprising a display device configured to:
   receive and display the first blood analyte level; and
   receive and display the corrected first blood analyte level.

5. The system of claim 4, wherein the display device is configured to:
   display the first blood analyte level until the corrected first blood analyte level is received; and
   after receiving the corrected first blood analyte level, display the corrected first blood analyte level instead of the first blood analyte level.

6. The system of claim 1, wherein the transceiver is further configured to:
   after receiving the second sensor data, receive third sensor data from the analyte sensor;
   calculate a third interstitial fluid analyte level using at least the third sensor data; and
   calculate the updated first interstitial fluid analyte level rate of change using at least the first interstitial fluid analyte level, the second interstitial fluid analyte level, the third interstitial fluid analyte level, and the one or more past interstitial fluid analyte levels.

7. A method of calculating and correcting blood analyte levels, the method comprising:
   using a transceiver to receive first sensor data from an analyte sensor;
   using the transceiver to calculate a first interstitial fluid analyte level based on at least the first sensor data;
   using the transceiver to calculate a first interstitial fluid analyte level rate of change based on at least the first interstitial fluid analyte level and one or more past interstitial fluid analyte levels;
   using the transceiver to calculate a first blood analyte level based on at least the first interstitial fluid analyte level and the first interstitial fluid analyte level rate of change;
   after receiving the first sensor data, using the transceiver to receive second sensor data from the analyte sensor;
   using the transceiver to calculate a second interstitial fluid analyte level based on at least the second sensor data;
   using the transceiver to calculate an updated first interstitial fluid analyte level rate of change based on at least the first interstitial fluid analyte level, the second interstitial fluid analyte level, and the one or more past interstitial fluid analyte levels; and
   using the transceiver to calculate a corrected first blood analyte level based on at least the first interstitial fluid analyte level and the first interstitial fluid analyte level rate of change.

8. The method of claim 7, further comprising:
   using the transceiver to calculate a second interstitial fluid analyte level rate of change based on at least the first and second interstitial fluid analyte levels; and
   using the transceiver to calculate a second blood analyte level based on at least the second interstitial fluid analyte level and the second interstitial fluid analyte level rate of change.

9. The method of claim 8, further comprising:
   using the transceiver to convey the first blood analyte level to a display device;
   using the transceiver to convey the second blood analyte level to the display device; and
   using the transceiver to convey the corrected first blood analyte level to the display device.

10. The method of claim 7, further comprising:
    using the transceiver to convey the first blood analyte level to a display device; and
    using the transceiver to convey the corrected first blood analyte level to the display device.

11. The method of claim 10, further comprising:
    using the display device to receive and display the first blood analyte level; and
    using the display device to receive and display the corrected first blood analyte level.

12. The method of claim 11, further comprising:
    using the display device to display the first blood analyte level until display device receives the corrected first blood analyte level; and
    using the display device to, after receiving the corrected first blood analyte level, display the corrected first blood analyte level instead of the first blood analyte level.

13. The method of claim 7, further comprising:
    after receiving the second sensor data, receiving third sensor data from the analyte sensor; and
    calculating a third interstitial fluid analyte level using at least the third sensor data;
    wherein calculating the updated first interstitial fluid analyte level rate of change uses at least the first interstitial fluid analyte level, the second interstitial fluid analyte level, the third interstitial fluid analyte level, and the one or more past interstitial fluid analyte levels.

14. A transceiver comprising:
    a sensor interface device configured to convey a power signal to an analyte sensor, receive first sensor data from the analyte sensor, and, after receiving the first sensor data, receive second sensor data; and
    a processor configured to:
       calculate a first interstitial fluid analyte level using at least the first sensor data;
       calculate a first interstitial fluid analyte level rate of change using at least the first interstitial fluid analyte level and one or more past interstitial fluid analyte levels;
       calculate a first blood analyte level using at least the first interstitial fluid analyte level and the first interstitial fluid analyte level rate of change;
       calculate a second interstitial fluid analyte level using at least the second sensor data;
       calculate an updated first interstitial fluid analyte level rate of change using at least the first interstitial fluid analyte level, the second interstitial fluid analyte level, and the one or more past interstitial fluid analyte levels; and
       calculate a corrected first blood analyte level using at least the first interstitial fluid analyte level and the first interstitial fluid analyte level rate of change.

15. The transceiver of claim 14, wherein the processor is further configured to:
    calculate a second interstitial fluid analyte level rate of change using at least the first and second interstitial fluid analyte levels; and
    calculate a second blood analyte level using at least the second interstitial fluid analyte level and the second interstitial fluid analyte level rate of change.

16. The transceiver of claim 15, further comprising a display interface device configured to:
    convey the first blood analyte level to a display device;
    convey the second blood analyte level to the display device; and
    convey the corrected first blood analyte level to the display device.

17. The transceiver of claim 14, further comprising a display interface device configured to:
   convey the first blood analyte level to a display device; and
   convey the corrected first blood analyte level to the display device.

18. The transceiver of claim 14, wherein the sensor interface device is further configured to, after receiving the second sensor data, receive third sensor data from the analyte sensor;
   wherein the processor is further configured to:
      calculate a third interstitial fluid analyte level using at least the third sensor data; and
      calculate the updated first interstitial fluid analyte level rate of change using at least the first interstitial fluid analyte level, the second interstitial fluid analyte level, the third interstitial fluid analyte level, and the one or more past interstitial fluid analyte levels.

19. A method of calculating and correcting levels in a first medium using measurements from a second medium, the method comprising:
   using a transceiver to calculate an initial second medium level based on at least initial measurement data;
   using the transceiver to calculate an initial second medium level rate of change based on at least the initial second medium level and one or more past second medium levels;
   using the transceiver to calculate a first medium level based on at least the initial second medium level and the initial second medium level rate of change;
   using the transceiver to calculate a subsequent second medium level based on at least subsequent measurement data;
   using the transceiver to calculate an updated second medium level rate of change based on at least the initial second medium level, the subsequent second medium level, and the one or more past second medium levels; and
   using the transceiver to calculate a corrected first medium level based on at least the initial second medium level and the updated second medium level rate of change.

20. The method of claim 19, further comprising:
   using the transceiver to calculate a subsequent second medium level rate of change based on at least the initial and subsequent second medium levels; and
   using the transceiver to calculate a subsequent first medium level based on at least the subsequent second medium level and the subsequent second medium level rate of change.

21. The method of claim 20, further comprising:
   using the transceiver to convey the first medium level to a display device;
   using the transceiver to convey the subsequent second medium level to the display device; and
   using the transceiver to convey the corrected first medium level to the display device.

22. The method of claim 19, further comprising:
   using the transceiver to convey the first medium level to a display device; and
   using the transceiver to convey the corrected first medium level to the display device.

23. The method of claim 22, further comprising:
   using the display device to receive and display the first medium level; and
   using the display device to receive and display the corrected first medium level.

24. The method of claim 23, further comprising:
   using the display device to display the first medium level until display device receives the corrected first medium level; and
   using the display device to, after receiving the corrected first medium level, display the corrected first medium level instead of the first medium level.

25. The method of claim 19, wherein the first medium is blood, and the second medium is interstitial fluid.

26. The method of claim 19, wherein the initial second medium level is an initial interstitial fluid analyte level.

27. A monitoring system for calculating and correcting levels in a first medium using measurements from a second medium, the system comprising:
   a sensor configured to take one or more measurements indicative of a level in the second medium; and
   a transceiver configured to:
      receive initial sensor data from the sensor, wherein the initial sensor data includes one or more measurements indicative of an initial level in the second medium;
      calculate an initial second medium level using at least the initial sensor data;
      calculate an initial second medium level rate of change using at least the initial second medium level and one or more past second medium levels;
      calculate a first medium level using at least the initial second medium level and the initial second medium level rate of change;
      receive subsequent sensor data from the sensor, wherein the subsequent sensor data includes one or more measurements indicative of a subsequent level in the second medium;
      calculate a subsequent second medium level using at least the subsequent sensor data;
      calculate an updated second medium level rate of change using at least the initial second medium level, the subsequent second medium level, and the one or more past second medium levels; and
      calculate a corrected first medium level using at least the initial second medium level and the updated second medium level rate of change.

28. The system of claim 27, wherein the transceiver is further configured to:
   calculate a subsequent second medium level rate of change based on at least the initial and subsequent second medium levels; and
   calculate a subsequent first medium level based on at least the subsequent second medium level and the subsequent second medium level rate of change.

29. The system of claim 28, wherein the transceiver is further configured to:
   convey the first medium level to a display device;
   convey the subsequent second medium level to the display device; and
   convey the corrected first medium level to the display device.

30. The system of claim 27, wherein the transceiver is further configured to:
   convey the first medium level to a display device; and
   convey the corrected first medium level to the display device.

31. The system of claim 30, further comprising the display device, wherein the display device is configured to:
   receive and display the first medium level; and
   receive and display the corrected first medium level.

32. The system of claim 31, wherein the display device is further configured to:
- display the first medium level until display device receives the corrected first medium level; and
- after receiving the corrected first medium level, display the corrected first medium level instead of the first medium level.

33. The system of claim 27, wherein the first medium is blood, and the second medium is interstitial fluid.

34. The system of claim 27, wherein the initial second medium level is an initial interstitial fluid analyte level.

* * * * *